United States Patent
Laron

(10) Patent No.: US 9,168,289 B2
(45) Date of Patent: Oct. 27, 2015

(54) METHOD OF TREATMENT OF SMALL FOR GESTATIONAL AGE INFANTS UNDER TWO YEARS OF AGE

(75) Inventor: Zvi Laron, Ramat Efal (IL)

(73) Assignee: MOR RESEARCH APPLICATIONS LTD., Tel Aviv (IL)

( * ) Notice: Subject to any disclaimer, the term of this patent is extended or adjusted under 35 U.S.C. 154(b) by 0 days.

(21) Appl. No.: 13/982,262

(22) PCT Filed: Jan. 31, 2012

(86) PCT No.: PCT/IL2012/000055
§ 371 (c)(1),
(2), (4) Date: Jul. 28, 2013

(87) PCT Pub. No.: WO2012/104838
PCT Pub. Date: Aug. 9, 2012

(65) Prior Publication Data
US 2013/0345132 A1    Dec. 26, 2013

Related U.S. Application Data

(60) Provisional application No. 61/438,334, filed on Feb. 1, 2011.

(51) Int. Cl.
A61K 38/18    (2006.01)
A61K 38/30    (2006.01)
A61K 38/27    (2006.01)
A61K 38/25    (2006.01)

(52) U.S. Cl.
CPC ............... *A61K 38/27* (2013.01); *A61K 38/25* (2013.01); *A61K 38/30* (2013.01)

(58) Field of Classification Search
None
See application file for complete search history.

(56) References Cited

U.S. PATENT DOCUMENTS

2007/0037861 A1 * 2/2007 Cutfield et al. ............... 514/356
2008/0070248 A1   3/2008 Parodi

OTHER PUBLICATIONS

Binder et al. Catch-up growth in autosomal dominant isolated growth hormone deficiency (IGHD type II). Growth Horm. & IGF Res. 17,242-248, 2007.*
Jung et al. Growth Hormone Treatment for Short Stature in Children Born Small for Gestational Age. Adv. Ther. 25, 951-978, 2008.*
Poduval et al., Safety and efficacy of growth hormone treatment in small for gestational age children. Cur. Op. Endocrin. 15, 376-382, 2008.*
Van Toledo-Eppinga et al. Effects of recombinant human growth hormone treatment in intrauterine growth-retarded preterm newborn infants on growth, body composition and energy expenditure, Acta Paediatr. 85, 476-81, 1996.*
Chatelain, P; "Children born small for gestational age or with very low-birth weight: clinical similarities and potential benefits of growth-hormone therapy," Pediatric Endocrinology Reviews, 6:514-518, 2009 (Abstract Only).
Lafeber, H, "Nutritional management and growth hormone treatment of preterm infants born small for gestational age," Acta Paediatrica Supplement, Nov. 1997.
Rasmussen, L, "Authentic recombinant human growth hormone results of a multicenter clinical trial in patients with growth hormone deficiency," Helvetica Paediatrica Acta, 43:443-448, 1988.
Shizume, K, "Long-term effects of human growth hormone on 1959 patients with pituitary dwarfism throughout Japan," Endocrinologica Japonica, 31:201-206, 1984.
Van Toledo-Eppinga et al., "Leucine and glucose kinetics during growth hormone treatment in intrauterine growth-retarded preterm infants," American J. of Phys., 270:E451-E455, 1996.

* cited by examiner

*Primary Examiner* — Elly-Gerald Stoica
(74) *Attorney, Agent, or Firm* — JMB Davis Ben-David

(57) ABSTRACT

The invention provides a method and a composition for the treatment of infants age less than 2.5 years old defined as small for gestational age (SGA), including the use of hGH or any compound that increases blood levels of hGH or of IGF-I. Early use of the composition prevents the irreversible neurological and psychological damage of the children.

11 Claims, No Drawings

METHOD OF TREATMENT OF SMALL FOR GESTATIONAL AGE INFANTS UNDER TWO YEARS OF AGE

CROSS-REFERENCE TO RELATED APPLICATIONS

This is the U.S. National Stage of International Application No. PCT/IL2012/000055, filed Jan. 31, 2012, which was published in English under PCT Article 21(2), which in turn claims the benefit of U.S. Provisional Patent Application No. 61/438,334, filed Feb. 1, 2011.

FIELD OF THE INVENTION

The present invention relates to methods for the treatment of infants defined as small for gestational age (SGA) by administration of hGH or of any compound that increases blood levels of at least one of hGH and IGF-I. More specifically, the invention relates to the treatment of said SGA infants by initiation of the hGH administration at the early age of under two years, thereby preventing irreversible future neurological and psychological damage.

BACKGROUND OF THE INVENTION

Small for gestational age (SGA) is defined as a birth weight less than 2 standard deviations (SD) below the $3^{rd}$ percentile. Between 2.5% to 10% of each population meet the criteria for SGA. This nomenclature is confusing and has therefore been contested [Laron Z., Ped. Endocrinol. Rev. 2009, 7(2):2], as small means also short.

Fetal growth restriction may occur early or late during fetal development. Infants who demonstrate reduced fetal growth early in gestation constitute approximately 20% of all SGA infants. They are symmetrically growth retarded: head circumference, weight, and length are proportionately affected to equivalent degrees. The Ponderal Index (weight divided by length cubed) or other body proportion ratios (head circumference to weight or length, femur length to abdominal circumference, head circumference to abdominal circumference) are used to detect symmetrical growth restriction during the fetal period [Verkauskiene R. et al., Eur J Endocrinol 2007; 157:606-12]. In addition to inherent genetic growth constraints, chromosomal disorders, congenital syndromes, IGF-1 (Insulin-Like Growth Factor-1) deficiency and early congenital viral infections, reduce the intrauterine growth rate at an early stage of development.

Intrauterine growth restriction may lead to infants being born SGA. SGA is associated with increased perinatal mortality and morbidity and postnatal growth failure [De Bie H. M. A. et al., Horm. Res. Paediatr. 2010, 73:6-14]. Fetal growth restriction is also associated with neuro-developmental pathology and contributes to late onset disorders such as cardiovascular disease, insulin resistance, and non insulin dependent diabetes [De Bie H. M. A. et al., Horm. Res. Paediatr. 2010, 73:6-14]. In addition, SGA children have decreased levels of intelligence and cognition, although the effects may be subtle [De Bie H. M. A. et al., Horm. Res. Paediatr. 2010, 73:6-14]. In four recent cohort studies, data was collected prospectively on pregnancy, birth and late developmental outcomes of large numbers of SGA term born infants. Strauss [Strauss R. S., J.A.M.A. 2000, 283:625-632] identified 1064 of 14189 term infants as SGA infants. Follow up at 5, 10, 16 and 26 years was 93%, 80%, 72% and 53% respectively. At follow-up (5-16 years), those born SGA demonstrated small but significant deficits in academic achievement. Teachers were less likely to rate them in the top 15% of the class at 16 years (13% vs 20%, P<0.01) and more likely to recommend special education (4.9% vs 2.3%, P<0.01) compared with those born at normal birth weight. At the age of 26 years, adults born SGA didn't demonstrate any difference in years of education, employment, marital status, or satisfaction with life. However, adults born SGA were less likely to have professional or managerial jobs (8.7% vs 16.4% P<0.01) and had significantly lower incomes. Larroque et al [Larroque B., Pediatrics 2001, 108:111-115] identified 218 SGA infants and 279 appropriate for gestational age (AGA) infants in a French cohort of 20,000 births born between 1971-1985. Late entry into secondary school was more frequent for SGA then AGA children. A significantly higher proportion of SGA adolescent failed to take or pass the baccalaureate examination than AGA adolescent. O'Keeffe et al [O'Keeffe M. J., Pediatrics 2003, 112:301-307] studied Australian children that were SGA or AGA infants and their mothers. Learning problems were present in 32% of the SGA group compared to 18% in the AGA group (p<0.001). The SGA group also performed inferiorly on the administered reading test, 22% vs 14% (p<0.001) in the AGA group. Lundgren et al. [Lundgren E. M. et al., Horm. Res. 2003, 59 (Suppl. 1):139-141] analyzed data from the Swedish Conscript Register. Intellectual and psychological performance was assessed. Low birth weight, short birth length, small head circumference and preterm birth increased the risk of subnormal intellectual and psychological performance. Among SGA the most important predictor was absence of catch-up growth.

Increasing evidence has shown that children born SGA, especially those born very small (short and underweight) suffer subsequently from neuro-developmental retardation and abnormalities [De Bie H. M. A. et al., Horm. Res. Paediatr. 2010, 73:6-14] and learning difficulties when reaching school age and even at later age [Tuvemo T. and Lundgren E. M., In: Kiess W, Chernausek S D, Hokken-Koelega A C S (eds.) Small for Gestational Age. Causes and Consequences. Basel, Karger, 2009:134-147]. A positive correlation between head circumference (HC), estimated brain weigh, and neurologic development during the first years has been shown [Sommerfelt K. et al., Arch. Dis. Child. 2000, 83:25-30; Gale C. R. et al., Brain 2004, 127:321-329; Gross S. J. et al., Am. J. Dis. Child. 1978, 132:753-756].

Congenital GH deficiency or GH insensitivity (Laron syndrome) result not only in reduced birth length, but also in a small HC [Laron Z., J. Clin. Endocrinol. Metab. 2004, 89:1031-1044; Laron Z. et al., In: Castells S, Wisniewski K E (eds). Growth Hormone Treatment in Down's Syndrome. John Wiley & Sons Ltd., 1993:151-161; Laron Z., Chapter 14. In: Rubin R T, Pfaff D, Eds. Hormone/behavior relations of clinical importance: Endocrine systems interacting with brain and behavior. Elsevier-Academic Press, New York, 2009, pp. 373-394] denoting retarded brain growth.

GH receptors (GH-R) and IGF-I receptors (IGF-IR) are present in wide parts of the brain. GH-R immunoreactivity is found in both neurons, astrocytes and oligodendrocytes [Lobie P. E. et al., Brain Res. Dev. Brain Res. 1993, 74:225-233]. Abundant GH-R expression is found in the choroid plexus. IGF-I-R is expressed in neuronal stem cells [Aberg M. A. et al., Mol. Cell. Neurosci. 2003, 24:23-40] but also present in neurons and glial cells throughout the brain [Chung Y. H. et al., Brain Res. 2002, 946:307-313].

The choroid plexus, which is a key area of the blood-brain-barrier (BBB), has abundance of GH-R and IGF-I-R as shown in both ligand-binding experiments [Araujo D. M. et al., Brain Res. 1989, 484:130-138] and from IGF-I-R mRNA studies [Aguado F. et al., J. Mol. Endocrinol. 1993, 11: 231-

239]. Apart from GH and IGF-I in the circulation there is a local synthesis of both GH and IGF-I in the brain outside the pituitary. IGF-I immunoreactivity is also widespread in all types of neurons in the brain [D'Ercole A. J. et al., Mol. Neurobiol. 1996, 13:227-255]. IGF-I expression in the CNS is particularly high during fetal development and peaks during the first 2 postpartum weeks, predominantly in neurons but also in glial progenitors [Bach M. A. et al., Brain Res. Mol. Brain Res. 1991, 10:43-48; Bartlett W. P., Brain Res. Mol. Brain Res. 1992, 12:285-291].

GH is taken up from the bloodstream into the brain parenchyma. GH-R is present in the choroid plexus which plays a role in the transport of GH across the BBB [Lai Z. N. et al., Brain Res. 1991, 546:222-226]. When GH was administered peripherally to patients with GH deficiency, a tenfold increase in GH in the cerebrospinal fluid was reported [Johansson J. O. et al., Neuroendocrinology 1995, 61:57-66].

It appears that IGF-I uptake is mediated by a specific carrier both in the capillary bed in the BBB [Duffy K R, Pardridge W M, Rosenfeld R G. Human blood-brain barrier insulin-like growth factor receptor. Metabolism 1988; 37:136-140] and in the blood-CSF barrier [Armstrong C. S. et al., J. Neurosci. Res. 2000, 59:649-660; Cam E. et al., J. Neurosci. 2005, 25:10884-10893].

It is important to note that local brain GH appears earlier in embryonic life than pituitary GH [Harvey S. and Hull K., J. Mol. Neurosci. 2003, 20:1-14]. In a rat model, postnatal brain development on days 6-27 following GH administration was enhanced [Diamond M. C., Brain Res. 1968, 7:407-418]. It appears that circulating GH and IGF-I has both cell proliferative and cell-survival promoting effects in the CNS [Aberg N. D. et al., Endocrinology 2007. 148:3765-3772]. IGF-I-R and estrogen-R interact in the promotion of neuronal survival and neuro-protection [Garcia-Segura L. M. et al., J. Neurocytology 2000, 29:425-437].

There are three major lines of evidence that support the notion of effects by GH/IGF-I on the human brain. First, the presence of the early GH and IGF-I system in the human brain has a similar appearance to that of rodents [Aberg N. D. et al., Scientific World J. 2006, 18; 6:53-80]. Accumulating studies show positive beneficial cognitive effects of GH substitution in GH-deficient patients [Falleti M. G. et al., Psychoneuroendocrinology 2006, 31:681-691]. With respect to neurogenesis, this phenomenon has been shown to occur in the adult human hippocampus [Eriksson P. S. et al., Nat. Med. 1998, 4:1313-1317].

Repeated testing of IQ and head circumference (HC) measurement in four children with congenital isolated growth hormone deficiency (IGHD) revealed a catch-up in both parameters in two patients treated at ages $3^{3/12}$ and $4^{5/12}$ but had no effect in two patients treated at ages $9^{1/12}$ and $13^{5/12}$ [Laron Z. and Galatzer A., Early Hum. Develop. 1981, 5:211-214]. Lagrou: et al [Lagrou K. et al., Eur. J. Endocrinol. 2007, 156:195-201] "Started hGH treatment in children at a mean age of 5.5±1.4"/2 years and found no effect. The inventors also found that initiation of hGH treatment of GHD children aged 2.9±1.4 years and a bone age of 1.2±0.9 years has faster and better effects on linear growth compared to children in whom treatment was started at a later age [Josefsberg Z. et al., Horm. Res. 1987, 27:126-133]. It should be explained that "bone age" is a way of describing the degree of maturation of the child's biological age. The "bone age" of a child is the average age at which children reach this stage of biological maturation. The inventors have also found that IGF-I treatment in Laron syndrome patients results in a fast catch-up growth of the HC [Laron Z. et al., Lancet 1992, 339:1258-1261].

The seemingly controversial effects of GH treatment on cognition [Siegel P. T. and Hopwood H. N., "The Relationship of Academic Achievement and the Intellectual Functioning and Affective Conditions of Hypopituitary Children". Hillsdale, N.J., Erlbaum, 1986; Sandberg D. et al., Children's Health Care 1998, 27:265-282; Smith M. O. et al., J. Dev. Behay. Pediatr. 1985, 6:273-278 (1990)], probably stems from the differences in diagnosis of these groups and from the age at treatment and from the biological age (bone age) at which treatment was initiated. Although very intriguing, the effects of GH or IGF-I therapy on neurogenesis (and other cell genesis) in naïve young animals have not been studied so far. This is an area of research which is very important, as the plasticity of the CNS seems to be greater in younger individuals.

Without being bound by theory, the inventors propose that the brain and its functions undergo a time-limited maturation during a relatively short period in-utero and in early postnatal life. This period is a window in which the developmental processes seem to respond to external factors. Thus, by early administration of GH to SGA patients under the age of two years, specifically, between about six-months to two years, the invention provides prevention of future neurological and psychological damage.

It is therefore an object of the invention to provide prophylactic methods for the treatment of small-for-gestational-age (SGA)-associated disorders, specifically, conditions associated with neurological damage, using growth hormone (GH) or any compound that increases blood levels of at least one of hGH and IGF-I, applied to SGA infants under two years of age.

In yet another object, the invention provides the use of GH for preventing SGA-associated disorders, specifically, conditions associated with neurological damage, in SGA infants under two years of age.

These and other objects of the invention will become apparent by the hand of the following description.

SUMMARY OF THE INVENTION

In the first aspect, the present invention provides a method for the treatment, amelioration, delaying the onset or prophylaxis of small-for-gestational-age (SGA)-associated disorders, diseases, conditions and sequelae. The method of the invention comprises the step of administering to an SGA subject in need thereof a therapeutically effective amount of a growth hormone (GH) or any derivative, conjugate, peptide or any fragment thereof, or of any compound that increases blood levels of at least one of hGH and IGF-I, or any composition comprising the same. It should be noted that the administration is initiated when the subject is under two years of age.

In the second aspect, the present invention relates to the use of a therapeutically effective amount of a growth hormone (GH) or any derivative, conjugate, peptide or any fragment thereof, or of any compound that increases blood levels of at least one of hGH and IGF-I, in the preparation of a composition for the treatment, amelioration, delaying the onset or prophylaxis of small-for-gestational-age (SGA)-associated disorders, diseases, conditions and sequelae, in a subject in need thereof. The treatment should be initiated when the SGA subject is under two years of age.

In the third aspect, the present invention provides a growth hormone (GH) or any derivative, conjugate, peptide or any fragment thereof, or any compound that increases blood levels of at least one of hGH and IGF-I or any composition comprising the same, for use in the treatment, amelioration, delaying the onset or prophylaxis of small-for-gestational-age (SGA)-associated disorders, diseases, conditions and sequelae, in an SGA subject in need thereof. According to this embodiment, the treated subject is under two years of age.

In the last aspect, the present invention provides a composition comprising a therapeutically effective amount of a growth hormone (GH) or any derivative, conjugate, peptide or any fragment thereof, or of any compound that increases blood levels of at least one of hGH and IGF-I, for use in the treatment, amelioration, delaying the onset or prophylaxis of small-for-gestational-age (SGA)-associated disorders, diseases, conditions and sequelae, in an SGA subject in need thereof. In specific embodiments, the treated subject is under two years of age. It should noted that the composition of the invention may optionally further comprise a pharmaceutically acceptable vehicle, diluent, excipient, hapten, adjuvant or additive.

DETAILED DESCRIPTION OF THE INVENTION

The present invention provides novel approach for preventing and treating SGA associated disorders, specifically, future neurological and psychological SGA-associated disorders by treating young infants, under the age of two years, with hGH or any compound that leads to elevation of hGH and/or IGF-I.

The term "small for gestational age" (SGA) describes a neonate whose birth weight or birth crown-heel length is at least 2 standard deviations (SD) below the mean SD) for the infant's gestational age, based on data derived from a reference population. SGA has also been defined in some publications as birth weight or length below the 10th, 5th, or 3rd percentile for gestational age. Although segregation of SGA from normal is somewhat arbitrary, ←2 SD was selected because it likely encompasses the majority of patients with disordered fetal growth and because most studies that have defined postnatal growth patterns and response to growth-promoting therapies have selected patients whose birth size is approximately −2 SD or less.

SGA babies may appear physically and neurologically mature but are smaller than other babies of the same gestational age. SGA babies may be proportionately small (equally small all over) or they may be of normal length and size but have lower weight and body mass. SGA babies may be premature (born before 37 weeks of pregnancy), full term (37 to 41 weeks), or post term (after 42 weeks of pregnancy).

Although some babies are small because of genetic factors (their parents are small), most SGA babies are small because of fetal growth problems that occur during pregnancy. Many babies with SGA suffered from a condition called intrauterine growth restriction (IUGR). IUGR occurs when the fetus does not receive the necessary nutrients and oxygen needed for proper growth and development of organs and tissues. IUGR can begin at any time in pregnancy. Early-onset IUGR is often due to chromosomal abnormalities, maternal disease, or severe problems with the placenta. Late-onset growth restriction (after 32 weeks) is usually related to other problems.

The condition is generally diagnosed by measuring the mother's uterus, with the fundal height being less than it should be for that stage of the pregnancy. If it is suspected, the mother will usually be sent for an ultrasound to confirm.

There are two distinct categories of growth restriction, indicating the stage at which the development was slowed. Small for gestational age babies can be classified as having symmetrical or asymmetrical growth restriction. Some conditions are associated with both symmetrical and asymmetrical growth restriction.

Symmetrical growth restriction, less commonly known as global growth restriction, indicates that the fetus has developed slowly throughout the duration of the pregnancy and was thus affected from a very early stage. The head circumference of such a newborn is in proportion to the rest of the body. Common causes include:

Early intrauterine infections, such as cytomegalovirus, rubella or toxoplasmosis
Chromosomal abnormalities
Anemia
Maternal substance abuse (prenatal alcohol use can result in Fetal alcohol syndrome)
Underdeveloped or maldeveloped placenta.

Asymmetrical growth restriction occurs when the embryo/fetus has grown normally for the first two trimesters but encounters difficulties in the third, usually secondary to preeclampsia. Such babies have a disparity in their length and head circumference when compared to the birth weight. A lack of subcutaneous fat leads to a thin and small body out of proportion with the head. Other symptoms include dry, peeling skin and an overly-thin umbilical cord. The baby is at increased risk of hypoxia and hypoglycaemia.

Causes Include:
Chronic high blood pressure
Severe malnutrition

Currently, treatment with hGH is indicated for SGA children, to improve their height deficit, only for those over the age of 2 years [Lee P. A. et al., Pediatrics, 2003 111(6):1253-1261], when the spontaneous postnatal catch-up phase is completed. Catch up growth is an acceleration of the growth rate following a period of growth retardation caused by a secondary deficiency, such as acute malnutrition or severe illness. The phenomenon, which routinely occurs in premature and SGA infants, involves rapid increase in weight, length, and head circumference and continues until the normal individual growth pattern is resumed, usually up to age 2. The severity, duration, and developmental timing at which the deficiency occurs may result in some growth inadequacy or permanent deficit, especially in such tissue as the brain.

Catch-up growth is characterized by height velocity above the limits of normal for age for at least 1 year after a transient period of growth inhibition; it can be complete or incomplete. Although catch-up growth can be expressed in terms of height velocity, the change in height standard deviation score is more appropriate. Catch-up growth is difficult to distinguish from the pubertal growth spurt. The increased growth rate following intrauterine growth retardation is usually called catch-up growth, although it does not meet all the criteria. It is not possible to know whether catch-up growth is complete for an individual child, but if final height is within the target range, it can be considered that catch-up growth has probably been complete.

As explained earlier, human Growth Homone (hGH) is currently indicated for the treatment of SGA children over the age of 2 years, i.e., once the catch up growth phase is complete. Growth hormone (GH) is a protein-based peptide hormone. It stimulates growth, cell reproduction and regeneration in humans and other animals. Growth hormone is a single-chain polypeptide that is synthesized, stored, and secreted by the somatotroph cells within the lateral wings of the anterior pituitary gland. Somatotropin refers to the growth hormone 1 produced naturally in animals, whereas the term somatropin refers to growth hormone produced by recombinant DNA technology, and is abbreviated "hGH" in humans. The release of GH is regulated by hypothtalamic hormones (GHRH) (GH releasing hormone) or its synthetic analogues, by Ghrelin, a GH stimulating peptide secreted by the hypothtlamus and stomach and by inhibitory hormone (somatostatin) secreted by the hypothalamus.

Growth hormone is used as prescription drug in medicine to treat children's growth disorders and adult growth hormone deficiency. Effects of growth hormone on the tissues of the body can generally be described as anabolic (building up). Like most other protein hormones, GH acts by interacting with a specific receptor on the surface of cells. Increased height during childhood is the most widely known effect of GH. Height appears to be stimulated by at least two mechanisms:

Because polypeptide hormones are not fat-soluble, they cannot penetrate sarcolemma. Thus, GH exerts some of its effects by binding to receptors on target cells, where it activates the MAPK/ERK pathway. Through this mechanism GH directly stimulates division and multiplication of chondrocytes of cartilage.

GH also stimulates, through the JAK-STAT signaling pathway, the production of insulin-like growth factor 1 (IGF-1, formerly known as somatomedin C), a hormone homologous to proinsulin. The liver is a major target organ of GH for this process and is the principal site of IGF-1 production. IGF-1 has growth-stimulating effects on a wide variety of tissues. Additional IGF-1 is generated within target tissues, making it what appears to be both an endocrine and an autocrine/paracrine hormone. IGF-1 also has stimulatory effects on osteoblast and chondrocyte activity to promote bone growth.

An important downstream effector of GH is IGF-1. IGF-1 is produced primarily by the liver as an endocrine hormone as well as in target tissues in a paracrine/autocrine fashion. Production is stimulated by growth hormone (GH) and can be retarded by undernutrition, growth hormone insensitivity, lack of growth hormone receptors, or failures of the downstream signalling pathway post GH receptor including SHP2 and STAT5B. IGF-1 is a primary mediator of the effects of growth hormone (GH). Growth hormone is made in the anterior pituitary gland, is released into the blood stream, and then stimulates the liver to produce IGF-1. IGF-1 then stimulates systemic body growth, and has growth-promoting effects on almost every cell in the body, especially skeletal muscle, cartilage, bone, liver, kidney, nerves, skin, hematopoietic cell, and lungs. In addition to the insulin-like effects, IGF-1 can also regulate cell growth and development, especially in nerve cells, as well as cellular DNA synthesis.

Deficiency of either growth hormone or IGF-1 therefore results in diminished stature. GH-deficient children are given recombinant GH to increase their size. IGF-1 deficient humans, who are categorized as having Laron syndrome, or Laron's dwarfism, are treated with recombinant IGF-1.

The inventors provide herein a method of treatment and prophylaxis, that improves both neural and cognitive development in SGA infants, as well as physical development in terms of height and weight, and prevents developmental defects or disorders associated with SGA by early administration of GH. Moreover, the proposed method improves future psychological and behavioral parameters in SGA children and prevents other SGA-related sequelae.

Thus, in the first aspect, the present invention provides a method for the treatment, amelioration, delaying the onset or prophylaxis of small-for-gestational-age (SGA)-associated disorders, diseases, conditions and sequelae. According to certain embodiments, the method of the invention comprises the step of administering to an SGA subject in need thereof a therapeutically effective amount of a growth hormone (GH) or any derivative, conjugate, peptide, analogue, homologue, mutant or fragment thereof, or of any compound that increases blood levels of at least one of hGH and IGF-I, or any composition comprising the same. An important feature of the invention is the initiation of administration when the subject is under two years of age.

As referred to herein, the term "treatment or prevention" relates to the complete range of therapeutically positive effects of administrating to a subject including inhibition, reduction of, alleviation of, and relief from, SGA associated disorders, defects and diseases symptoms or undesired side effects thereof. More specifically, treatment or prevention includes the prevention or attentuation of development of the disease, prevention or postponement of development of symptoms and/or a reduction in the severity of such symptoms that will or are expected to develop. These further include ameliorating existing symptoms, preventing additional symptoms and ameliorating or preventing the underlying causes of symptoms.

SGA infants suffer from abnormal development, leading to a wide spectrum of disorders. The method of the invention is particularly suitable for the treatment of such infants, wherein the SGA-associated disorders, diseases and sequelae are at least one of neurological, psychological, cognitive and behavioral damage, disorders or conditions.

The method of the invention is also effective in SGA infants, wherein the SGA-associated disorders, diseases and sequelae further comprise at least one of weight, height and head circumference being under at least 2 standard deviations (SD).

It is understood that the interchangeably used terms "associated" and "related", when referring to pathologies herein, mean diseases, disorders, conditions, or any pathologies which at least one of: share causalities, co-exist at a higher than coincidental frequency, or where at least one disease, disorder condition or pathology causes the second disease, disorder, condition or pathology.

Non-limiting examples of diseases and disorders associated with SGA comprise: neural, cognitive and behavioral developmental disorders, short stature, acromicria and organomicria, hypoglycemia, necrotizing enterocolitis (NEC), intraventricular hemorrhage (IVH), periventricular leukomalacia, hearing loss, hypothermia, apnea of prematurity, metabolic acidosis, hypernatremia, nonoliguric hyperkalemia, compromised renal function, pulmonary disease, sepsis, hyperbilirubinemia, cholestasis, elevated triglyceride levels, kernicterus, hypocalcemia, respiratory distress syndrome (RDS), air leak syndromes, chronic lung disease, brachiopulmonary disorder (BPD), retinopathy of prematurity (ROP), patent ductus arteriosis (PDA), hypoxia, infection and anemia. Indeed, certain embodiments of the methods of treatment according to the invention contemplate the treatment of these SGA-associated diseases and disorders.

According to certain embodiments, the method of the invention is contemplated, wherein the SGA subject is between about two months to about two years old.

According to more specific embodiments of the method of the invention, the SGA subject is under one year of age. More specifically, the SGA subject is between about three months to about one year old. Furthermore, according some embodiments of the method of the invention, the subject is at least six months old.

Without being bound by theory, the inventors postulate that early administration of GH to SGA infants under two years of age is likely to improve various developmental parameters, including significantly enhancing neurological, psychological and cognitive outcomes.

It should be appreciated that the method of the invention is especially effective in the treatment of subjects which did not present a catch up growth at the age of about six months. The method of the invention is particularly useful in SGA infants wherein the subject birth weight is between about 1200 to about 2200 grams. According to more specific embodiments, the method of the invention is applicable in subjects presenting with symmetrical SGA.

Using GH for the treatment of SGA infants according to the invention yields tangible developmental benefits. It is appreciated that the treatment method improves at least one of Bayley Scales of Infant Development examination score, formal neurological examination score, Pediatric Quality of Life Inventory score and Achenbach Child Behavior Checklist score.

The Bayley Scales of Infant Development (BSID-III is the current version) is a standard series of measurements used primarily to assess the motor (fine and gross), language (receptive and expressive), and cognitive development of infants and toddlers, ages 0-3. This measure consists of a series of developmental play tasks and takes between 45-60 minutes to administer. Raw scores of successfully completed items are converted to scale scores and to composite scores. These scores are used to determine the child's performance compared with norms taken from typically developing children of their age (in months). The assessment is often used in conjunction with the Social-Emotional Adaptive Behavior Questionnaire. Completed by the parent or caregiver, this questionnaire establishes the range of adaptive behaviors that the child can currently achieve and enables comparison with age norms.

The PedsQL measure is a measure of health-related quality of life in children by parent proxy-reports, and the scale forms are modified to be developmentally appropriate for children ages 2-4 years.

Achenbach Child Behavior Checklist (The Child Behavior Checklist (CBCL)) is a widely-used method of identifying problem behavior in children. It is a component in the Achenbach System of Empirically Based Assessment. Problems are identified by a respondent who knows the child well, usually a parent or teacher. There are two versions of the checklist. The preschool checklist (CBCL/1½-5) is intended for use with children aged 18 months to 5 years. The school-age version (CBCL/6-18) is for children aged 6 to 18 years. The checklists consist of a number of statements about the child's behavior, e.g. acts too young for his/her age. Responses are recorded on a Likert scale: 0=Not True, 1=Somewhat or Sometimes True, 2=Very True or Often True. The preschool checklist contains 100 questions and the school-age checklist contains 120 questions.

In some embodiments of the method of the invention, the administration is continued for duration of between about one to about five years, and in more specific embodiments, the administration is continued for duration of up to two years.

According to some embodiments of the method of the invention, the therapeutically effective amount ranges between about 1 µg/kg/day to about 100 µg/kg/day, about 5 µg/kg/day to about 90 µg/kg/day, about 10 µg/kg/day to about 80 µg/kg/day, about 15 µg/kg/day to about 70 µg/kg/day, about 20 µg/kg/day to about 60 µg/kg/day. More specifically, about 20 µg/kg/day to about 50 µg/kg/day, whereas in more specific embodiments, the therapeutically effective amount ranges between about 25 to about 35 µg/kg/d.

In another aspect, the invention provides the use of a therapeutically effective amount of a growth hormone (GH) or any derivative, conjugate, peptide, analogue, homologue, mutant or fragment thereof, or of any compound that increases blood levels of at least one of hGH and IGF-I, in the preparation of a composition for the treatment, amelioration, delaying the onset or prophylaxis of small-for-gestational-age (SGA)-associated disorders, diseases, conditions and sequelae, in a subject in need thereof. According to certain embodiments, administration is initiated when the subject is under two years of age.

It is appreciated that for prophylaxis, a prophylactically effective amount of GH is administered. The term "prophylactically effective amount" is intended to mean that amount of a compound or a pharmaceutical composition comprising it, that will prevent or reduce the risk of occurrence or development of the biological or medical event that is sought to be prevented in a tissue, a system, animal or human by a researcher, veterinarian, medical doctor or other clinician. In prophylactic applications, the compositions of the invention are administered to a patient who is either exhibiting initial symptoms of the disorder or at risk of developing the disorder to enhance the patient's resistance. Such an amount is defined to be a "prophylactically effective dose". In this use, the precise amounts again depend upon the patient's state of health and general level of immunity, but generally range from 0.001 to 100 mg (1 µg to 100 mg) per dose, or more specifically, between about 5 µg to about 90 µg, between about 10 µg to about 80 µg, between about 15 µg to about 70 µg, between about 20 µg to about 60 µg, between about 20 µg to about 50 µg, between about 20 µg to about 40 µg, or between about 25 µg to about 35 µg.

The present invention provides the use of (GH) or any derivative, conjugate, peptide, analogue, homologue, mutant or fragment thereof or of any compound that increases blood levels of at least one of hGH and IGF-I, in the preparation of prophylactic compositions for preventing or inhibiting SGA-associated neurological and psychological damage in SGA subjects. The terms "prevention", "inhibition", "moderation" or "attenuation" as referred to herein, relate to the retardation, restraining or reduction of at least one of neurological, psychological, behavioral and cognitive damage, disorder, disease or condition in the treated subject. Such reduction includes reduction by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

With regards to the above, it is to be understood that, where provided, percentage values such as, for example, 10%, 50%, 120%, 500%, etc., are interchangeable with "fold change" values, i.e., 0.1, 0.5, 1.2, 5, etc., respectively.

The use of the invention is particularly suitable for the treatment of SGA infants, wherein the SGA-associated disorders, diseases and sequelae are at least one of neurological, psychological, cognitive and behavioral damage, disorders or conditions.

The use of the invention is also effective in SGA infants, wherein the SGA-associated disorders, diseases and sequelae further comprise at least one of weight, height and head circumference being under at least 2 standard deviations (SD).

According to one embodiment of the use of the invention, the SGA-associated disorders, diseases and sequelae may further comprise at least one of neural, cognitive and behavioral developmental disorders, short stature, acromicria and organomicria, hypoglycemia, necrotizing enterocolitis (NEC), intraventricular hemorrhage (IVH), periventricular leukomalacia, hearing loss, hypothermia, apnea of prematurity, metabolic acidosis, hypernatremia, nonoliguric hyperkalemia, compromised renal function, pulmonary disease, sepsis, hyperbilirubinemia, cholestasis, elevated triglyceride levels, kernicterus, hypocalcemia, respiratory distress syndrome (RDS), air leak syndromes, chronic lung disease, brachiopulmonary disorder (BPD), retinopathy of prematurity (ROP), patent ductus arteriosis (PDA), hypoxia, infection and anemia.

According to certain embodiments, the use of the invention is contemplated, wherein the SGA subject is between about two months to about two years old. More specifically, the treated subject may be an infant in the age of about 2, 3, 4, 5, 6, 7, 8, 9, 10, 12, 13, 14, 15, 16, 17, 18, 19, 20, 21, 22, 23 or 24 months old.

According to more specific embodiments of the use of the invention, the SGA subject is under one year of age. More specifically, the SGA subject is between about three months to about one year old. Furthermore, according some embodiments of the use of the invention, the subject is at least six months old.

It is understood that the use of the invention is effective in the treatment of subjects which did not present a catch up growth at the age of about six months. The use of the invention is particularly helpful in SGA infants wherein the subject birth weight is between about 1000 to about 2500 grams, more specifically, about 1200 to about 2200 grams. According to specific embodiments, the use of the invention is applicable in subjects presenting with symmetrical SGA.

It is appreciated that the use of the invention results in the improvement of at least one of Bayley Scales of Infant Development examination score, formal neurological examination score, Pediatric Quality of Life Inventory score and Achenbach Child Behavior Checklist score.

In some embodiments of the use of the invention, the administration is continued for duration of between about one to about five years, and in more specific embodiments, the administration is continued for duration of up to two years.

According to some embodiments of the use of the invention, the therapeutically effective amount ranges between about 20 µg/kg/day to about 50 µg/kg/day, whereas in more specific embodiments, the therapeutically effective amount ranges between about 25 to about 35 µg/kg/d. However, it is understood that these ranges may differ considerably according to the patient physiological sate and reaction to treatment, as may be readily determined by medical staff. For example, the daily dosage may be about 1 to about 150 µg/kg/d, about 5 to about 120 µg/kg/d, about 10 to about 100 µg/kg/d, about 15 to about 80 µg/kg/d, about 16 to about 60 µg/kg/d, about 17 to about 55 µg/kg/d, about 18 to about 53 µg/kg/d, about 19 to about 51 µg/kg/d, or more specifically about 20 to about 50 µg/kg/d.

In a further aspect, the invention relates to a growth hormone (GH) or any derivative, conjugate, peptide, analogue, homologue, mutant or fragment thereof, or of any compound that increases blood levels of at least one of hGH and IGF-I, or any composition comprising the same, for use in the treatment, amelioration, delaying the onset or prophylaxis of small-for-gestational-age (SGA)-associated disorders, diseases, conditions and sequelae, in an SGA subject in need thereof. The subject is under two years of age.

The growth hormone used by the present invention may be a recombinant and/or purified GH. The term "purified" refers to molecules, such as amino acid sequences, or peptides that are removed from their natural environment, isolated or separated. An "isolated peptide" is therefore a purified amino acid sequence. "Substantially purified" molecules are at least 60% free, preferably at least 75% free, and more preferably at least 90% free from other components with which they are naturally associated. As used herein, the term "purified" or "to purify" also refers to the removal of contaminants from a sample.

As stated, this aspect of the invention relates not only to growth hormone (GH) per se, but also or of any compound that increases blood levels of at least one of hGH and IGF-I, or any derivative, conjugate, peptide, analogue, homologue, mutant or fragment thereof, including IGF-1 itself, for use in the treatment, amelioration, delaying the onset or prophylaxis of small-for-gestational-age (SGA)-associated disorders, diseases, conditions and sequelae in an SGA subject. IGF-1 blood level is increased in direct response to GH, however, the art describes various compounds and compositions which enhance GH and/or IGF-1 blood level, either directly or indirectly. Non-limiting examples of such compounds comprise: GHRH and analogues thereof (GH releasing hormone), GHRP-2 and GHRP-6 (GH releasing peptide 2 and 6), Hexarelin, Pralmorelin etc., Ghrelin and its analogues, triiodothyronine (T3), testosterone, isoflavones, capsaicin, casein, bovine colostrum and zinc.

Some specific commercial hGH formulations that may be particularly suited for the invention comprise, but are not limited to: Somatropin (191 Amino Acid Sequence hGH) formulations such as Nutropin and Genotropin (Genentech), Humatrope (Eli Lilly), Norditropin (Novo Nordisk), Saizen, Serostim and Zorbtive (Serono), Hypertropin (NeoGenica) and Jintropin (GeneScience), and Somatrem (192 Amino Acid Sequence hGH or Met-hGH) such as Tev-Tropin (TEVA Pharmaceutical), Ansomone (AnkeBio) and Fitropin (Kexing), Omnitrope (Sandoz), Protropin (Somatrem; Genentech-Roche) and Zomacton (Ferring Pharmaceuticals).

Commercial IGF-1 formulations are also available and may be used according to the invention. For example, Increlex (generic name: Mecasermin; produced by Tercica, Inc.).

Commercial formulations of GH releasing peptides (GHRP), which induce GH secretion (secretagogues), are also available and may be used according to the invention. For example Pralmorelin (also known as GPA 748, GHRP 2, growth hormone-releasing peptide 2, KP-102 D and KP 102 LN; produced by Kaken, Japan and Wyeth).

It is understood that GH releasing hormone (GHRH; also known as GRF, GHRF or somatocrinin) formulations are also considered useful according to some embodiments of the invention.

Still further, as indicated above, the invention relates to growth hormone (GH) or any derivative, conjugate, peptide, analogue, homologue, mutant or fragment thereof, or of any compound that increases blood levels of at least one of hGH and IGF-I. The term "analogues" used herein refers to those polypeptides which may be obtained by alteration, substitution or modification of one or more amino acid residue(s) in the sequence of said growth hormone (GH), and/or IGF-1 or any modulating compound. A "fragment" of a GH molecule, is meant to refer to any amino-acid subset of the molecule. A "derivative" or "fragment" may be any amino acid subset of these sequences having any insertions, deletions, substitutions and modifications to the amino acid sequences of GH, that do not interfere with the ability of GH to induce blood IGF-1 levels in SGA patients. A derivative should maintain a certain homology to said amino acid sequence, e.g. at last 70%. Homologues of GH refer to proteins, in which one or more of the amino acid residues of a natural GH are replaced by different amino acid residues, or are deleted, or one or more amino acid residues are added to the natural sequence of leptin, without changing considerably the activity of the resulting products as compared with the wild type GH. These homologues are prepared by known synthesis and/or by site-directed mutagenesis techniques, or any other known technique suitable therefore. Any such homologue preferably has a sequence of amino acids sufficiently duplicative of that of GH, such as to have substantially similar activity to GH. One such activity is the ability of a GH homologue to induce an increase in blood IGF-1 level. Thus, it can be determined whether any given homologue has substantially the same activity as GH by means of routine experimentation. The "mutants" according to the invention may have at least one mutation selected from the group consisting of point mutations, missense, nonsense, insertions, deletions or rearrangement in the GH polypeptide, while maintaining its function, which is the induction of an increase in blood IGF-1 level. It should be appreciated that the term "insertions" or "deletions" as used herein is meant any addition or reduction, respectively, of amino acid residues to the sequences of GH (Genbank accession nos. AAA98618, P01241, CAA23779, CAA00065, AAA35891, CAA01211, CAA00068 and AAA98618) or IGF-1 (Genbank accession nos. CAA01954, CAA01955, CAA40093, CAA40092, CAA24998, or NCBI Reference Sequences NP_001104755, NP_001104754, NP_001104753 and NP_000609), between about 1 to 10 amino acid residues and most preferably, addition or alternatively deletion of 1, 2, 3, 4, 5, 6, 7, 8, 9 or 10 amino acid residues to the sequence of the invention. In some places, the term "functional" is added to the terms "fragment", "derivative" and "homologue". This indicates that the "fragment", "derivative" or "homologue" maintain, or at least partially maintains its original biological activity. It is important to mention that some of the provided Genbank accession numbers refer to the GH precursor having 217 aa, which is processed into the mature 191 aa form, and is the active hormone.

The (GH) or any compound that increases hGH and/or IGF-1 blood level, or any derivative, conjugate, peptide, analogue, homologue, mutant or fragment thereof, or any composition comprising the same, for use in the treatment, amelioration, delaying the onset or prophylaxis of small-for-gestational-age (SGA)-associated disorders, diseases, conditions and sequelae of the invention is particularly suitable for the treatment of SGA infants, wherein the SGA-associated disorders, diseases and sequelae are at least one of neurological, psychological, cognitive and behavioral damage, disorders or conditions. In other embodiments, it is effective in SGA infants, wherein the SGA-associated disorders, diseases and sequelae further comprise at least one of weight, height and head circumference (HC) being under at least 2 standard deviations (SD).

According to one embodiment of the GH of the invention, the SGA-associated disorders, diseases and sequelae may further comprise at least one of neural, cognitive and behavioral developmental disorders, short stature, acromicria and organomicria, hypoglycemia, necrotizing enterocolitis (NEC), intraventricular hemorrhage (IVH), periventricular leukomalacia, hearing loss, hypothermia, apnea of prematurity, metabolic acidosis, hypernatremia, nonoliguric hyperkalemia, compromised renal function, pulmonary disease, sepsis, hyperbilirubinemia, cholestasis, elevated triglyceride levels, kernicterus, hypocalcemia, respiratory distress syndrome (RDS), air leak syndromes, chronic lung disease, brachiopulmonary disorder (BPD), retinopathy of prematurity (ROP), patent ductus arteriosis (PDA), hypoxia, infection and anemia.

According to certain embodiments, the GH of the invention is contemplated, wherein the SGA subject is between about two months to about two years old. According to more specific embodiments of the GH of the invention, the SGA subject is under one year of age. More specifically, the SGA subject is between about three months to about one year old. Yet more specifically, according some embodiments of the GH of the invention, the subject is at least six months old.

It is understood that the GH of the invention is effective in the treatment of subjects which did not present a catch up growth at the age of about six months. The method of the invention is particularly useful in SGA infants wherein the subject birth weight is between about 1200 to about 2200 grams. According to particular embodiments, the GH of the invention is applicable in subjects presenting with symmetrical SGA.

It is appreciated that the GH of the invention improves at least one of Bayley Scales of Infant Development examination score, formal neurological examination score, Pediatric Quality of Life Inventory score and Achenbach Child Behavior Checklist score.

In some embodiments of the GH of the invention, the administration is continued for duration of between about one to about five years, and in more specific embodiments, the administration is continued for duration of up to two years.

According to some embodiments of the GH of the invention, the therapeutically effective amount ranges between about 20 µg/kg/day to about 50 µg/kg/day, whereas in more specific embodiments, the therapeutically effective amount ranges between about 25 to about 35 µg/kg/d, but it is understood that these ranges may differ considerably according to the patient physiological sate and reaction to treatment, as may be readily determined by qualified medical staff. For example, the daily dosage may be about 1 to about 150 µg/kg/d, about 5 to about 120 µg/kg/d, about 10 to about 100 µg/kg/d, about 15 to about 80 µg/kg/d, about 16 to about 60 µg/kg/d, about 17 to about 55 µg/kg/d, about 18 to about 53 µg/kg/d, about 19 to about 51 µg/kg/d, or more specifically about 20 to about 50 µg/kg/d.

In the last aspect, the invention relates to a composition comprising a therapeutically effective amount of a growth hormone (GH) or any compound that increases IGF-1 blood level, or any derivative, conjugate, peptide, analogue, homologue, mutant or fragment thereof, or any composition comprising the same, for use in the treatment, amelioration, delaying the onset or prophylaxis of small-for-gestational-age (SGA)-associated disorders, diseases, conditions and sequelae, in an SGA subject in need thereof, wherein the subject is under two years of age, the composition optionally further comprises a pharmaceutically acceptable vehicle, diluent, excipient, hapten, adjuvant or additive.

The present invention further provides a composition comprising a therapeutically effective amount of a growth hormone (GH) or any derivative, conjugate, peptide, analogue, homologue, mutant or fragment thereof, or of any compound that increases blood levels of at least one of hGH and IGF-I for use in the treatment, amelioration, delaying the onset or prophylaxis of small-for-gestational-age (SGA)-associated disorders, diseases, conditions and sequelae. It should be noted that the composition of the invention is used for treating SGA subjects that are under two years of age. As mentioned herein before, the compositions provided by the invention optionally further comprise at least one pharmaceutically acceptable excipient or vehicle. As used herein "pharmaceutically acceptable vehicle" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

The pharmaceutical forms suitable for injection use include sterile aqueous solutions or dispersions that may be freeze-dried and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms, such as bacteria and fungi.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above.

In the case of sterile powders for the preparation of the sterile injectable solutions, the preferred method of preparation are vacuum-drying and freeze drying techniques which yield a powder of the active ingredient plus any additional desired ingredient from a previously sterile-filtered solution thereof.

Pharmaceutical compositions used to treat subjects in need thereof according to the invention generally comprise a buffering agent, an agent who adjusts the osmolarity thereof, and optionally, one or more pharmaceutically acceptable vehicles, excipients and/or additives as known in the art. Supplementary active ingredients can also be incorporated into the compositions. The vehicle can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

In various embodiments, the final solution may be adjusted to have a pH between about 4 and about 9, between about 5 and about 7, between about 5.5 and about 6.5, or about 6. The pH of the composition may be adjusted with a pharmacologically acceptable acid, base or buffer.

Intranasal formulations are well known in the art and can either be powder formulations, or more commonly nasal sprays. Such sprays typically comprise a solution of the active drug in physiological saline or other pharmaceutically suitable carrier liquids. Various nasal spray compression pumps are also well known in the art and can be calibrated to deliver a predetermined dose of the active drug.

The pharmaceutical composition of the invention can be administered and dosed by the methods of the invention, in accordance with good medical practice, systemically, for example by parenteral, e.g. intravenous, intraperitoneal or intramuscular injection. In another example, the pharmaceutical composition can be introduced to a site by any suitable route including intravenous, subcutaneous, transcutaneous, topical, intramuscular, intraarticular, subconjunctival, or mucosal, e.g. oral, intranasal, or intraocular administration.

More specifically, the compositions used in the methods of the invention may be adapted for administration by parenteral, intraperitoneal, transdermal, oral (including buccal or sublingual), and any other appropriate routes. Such formulations may be prepared by any method known in the art of pharmacy, for example by bringing into association the active ingredient with the vehicle (s) or excipient(s).

Compositions and formulations for oral administration include powders or granules, suspensions or solutions in water or non-aqueous media, capsules, sachets, lozenges (including liquid-filled), chews, multi- and nano-particulates, gels, solid solution, liposome, films, ovules, sprays or tablets. Thickeners, flavoring agents, diluents, emulsifiers, dispersing aids or binders may be desirable.

Pharmaceutical compositions used to treat subjects in need thereof according to the invention, which may conveniently be presented in unit dosage form, may be prepared according to conventional techniques well known in the pharmaceutical industry. Such techniques include the step of bringing into association the active ingredients with the pharmaceutical vehicle(s) or excipient(s). In general formulations are prepared by uniformly and intimately bringing into association the active ingredients with liquid vehicles or finely divided solid vehicles or both, and then, if necessary, shaping the product. The compositions may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers. The pharmaceutical compositions of the present invention also include, but are not limited to, emulsions and liposome-containing formulations.

It should be understood that in addition to the ingredients particularly mentioned above, the formulations may also include other agents conventional in the art having regard to the type of formulation in question, for example those suitable for oral administration may include flavoring agents.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Unless defined otherwise, all technical and scientific terms used herein have the same meaning as commonly understood by one of ordinary skill in the art to which this invention is related. The following terms are defined for purposes of the invention as described herein.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

Population

Near-term (≥34 weeks) and term SGA infants. The population of SGA infants is approximately 2.5% of all newborns. The inventors estimate that 25-30% of SGA infants are symmetrically SGA. At the Rabin Medical Center there are approximately 9000 deliveries per year. Assuming that 1% of these deliveries are symmetrical SGA, the expected population to be screened would be 90 infants per year. Of these infants approximately half will be excluded, leaving around 50 infants. Of these 50 infants, many will demonstrate catch-up growth leaving about 20-25 eligible infants per year for inclusion in the study. As the enrolment will last for two years, the study population will be double. If one wishes to double or triple the test population, one or more Tel Aviv University affiliated centers can easily be included.

Inclusion Criteria

Symmetrical small for gestational age at birth: weight, length and head circumference all below −2 SD for gestational age.

Birth weight of 1200-2200 gr

Follow-up of growth until age of 6-12 months

Growth parameters below −2 SD at age of 6-12 months and absence of sufficient catch-up.

Exclusion Criteria

Chromosomal aberration

Congenital syndrome

Major congenital malformation (affecting growth or development)

Congenital infection

Exposure to teratogenic drugs or drugs affecting development during pregnancy

Maternal drug or alcohol abuse.

Maternal cancer.

Maternal diabetes mellitus.

Control Groups

As controls serve the infants whose parents do not agree to the hGH trial.

Statistical Evaluation

A biostatistician of Schneider Children's Medical Center is available to perform the statistical analysis for the study.

Duration of Study

Subjects are enrolled during a 2-year period. Subjects are initially identified from admission records of the Neonatal Department and Delivery Room, Rabin Medical Center. Eligibility for enrolment is determined by a follow-up telephone call at 6 months of age. Follow-up is completed 2-2.5 years after enrolment of last subject.

Clinical Data Collection

Clinical data collection includes the following methods:

Socioeconomic questionnaire that includes maternal and paternal occupation and number of years of formal education completed.

Maternal and paternal biometrics medical history that includes age, weight, height, BMI, head circumference, and history of chronic illnesses.

Obstetrical and neonatal risk questionnaire that includes pregnancy complications, prenatal ultrasound data, labor and delivery, Apgar scores, neonatal complications.

Infant's biometric data at birth and during each study visit: weight, length, head circumference.

Cognitive, Neurological, Psychological, Quality of Life and Behavior Assessment

All examiners are blinded to the original study groups. The outcomes are determined from the scores of neurological and cognitive assessments. The neurological and cognitive examinations are as follows:

Cognitive Assessments

Cognitive assessments are performed by a certified child psychologist that administers the Bayley Scales of Infant Development, 3rd edition (BSID-III).

This clinical instrument is widely used for assessing the development of infants and children 1 month through 42 months old. The BSID-II, [Bayley N., Bayley Scales of Infant Development. Second ed. San Antonio, Tex.: The Psychological Corporation; 1993] originally published in 1993, includes mental, motor, and behavior rating scales. For the present study the inventors use the BSID-III, [Bayley N., (2006), Bayley Scales of Infant Development, 3rd Ed. The Psychological Corporation, New York, N.Y.] published in 2006. This newer version provides a more detailed developmental assessment that includes three sub-domains scales to assess cognitive, motor, and language skills, and two parent questionnaires (social-emotional and adaptive behavior). Both versions of the bayley scales were developed using normative samples of 1700 US children. Reliability and validity are reported in the test manuals [Bayley N. Bayley Scales of Infant Development. Second ed. San Antonio, Tex.: The Psychological Corporation, 1993; Bayley N. (2006), Bayley Scales of Infant Development, 3rd Ed. The Psychological Corporation, New York, N.Y.]. This Bayley Scales of Infant Development consists of a series of developmental tasks and takes 45-60 minutes to administer. Raw scores are converted to scale scores and to composite scores that are compared with published age norms. From the administered scale, at each of the 3 study visits, scores are calculated for the following subtests: (A) cognition, (B) language (a-expressive, b-receptive), (C) Motor (a-fine motor, b-gross motor). From the caregiver questionnaires, scores are calculated for the (D) Social emotional and (E) Adaptive Behavior domains.

Neurologic Status

Neurologic status is evaluated using a formal neurological examination, which includes assessment of cranial size, cranial nerves, special senses, and motor function (i.e., deep tendon reflexes, muscle tone, muscle strength, coordination, and gait). The findings are then categorized as normal, suspect, or abnormal.

The PedsQL Measure

The PedsQL measure [Varni J. W. et al., Med. Care 2001, 39:800-812] is administered to assess the quality of life of children. The Pediatric Quality of Life Inventory (PedsQL™ 4.0) is a measure of health-related quality of life in children by parent proxy-reports, and the scale forms are modified to be developmentally appropriate for children ages 2-4 years. This measure evaluates difficulties in functioning in (A) physical, (B) emotional, (C) social, and (D) school domains. Each items is linearly transformed to a 0-100 scale that can be compared to normative means of subscale scores.

Achenbach Child Behavior Checklist

The Child Behavior Checklist (CBCL) is used to measure behavioral development. The CBCL includes 113 items and caregiver's report on the frequency of each behavior over the past 6 months (0=not true, 1=somewhat or sometimes true, 2=very true or often true). Scores are summed to yield externalizing and internalizing problem behavior scores.

Example 1

Assessment of Early Growth Hormone Treatment of SGA Clinical Outcome

The inventors hypothesize that early hGH administration to SGA infants may improve both physical and cognitive development. Thus, the inventors designed the following experimental procedure to assess the effect of early growth hormone treatment given to symmetrical small for gestational age (SGA) infants not demonstrating catch-up growth, on neurodevelopment and growth between birth and 6-12 months of age.

The inventors opt for a multi-center trial of early gowth hormone treatment. Infants are identified after birth. At the age of 6 months, infants who do not demonstrate sufficient catch-up growth are eligible for enrolment in the study. Following informed consent by the parents, treatment with growth hormone is initiated at the age of 6-12 month and given for a period of 2 years. The study cohort of infants receiving growth hormone is compared to the cohort of infants eligible for inclusion, but for whom consent was obtained for developmental follow-up only.

The experiment timeline is summarized in Table 1 below. The experimental and control populations are selected as described in the Experimental Procedures section. The study is initiated with collection of clinical data, including a socio-economic questionnaire, maternal and paternal biometrics, medical history, obstetrical and neonatal risk questionnaire and infant biometric data, as described in the procedures section. A Bayley Scales of Infant Development test is also administered at baseline time point.

The experimental group is administered with an initial dose of 0.033 mg/kg/d. The dose is adjusted by monitoring the serum IGF-I level. The aim is to obtain levels between 150-250 ng/ml. The duration of hGH treatment is 2 years.

An anthropometric follow-up (length, weight and head circumference) is performed every 3-4 months during the first year of age and every 4 months during hGH treatment and every 6 months until the age of 4 years. Prolongation of follow-up including auxiological and neuro-developmental parameters of the hGH treated and control infants is possible using age-appropriate tests. Long-term follow-up of the treated infants for possible late adverse effects of hGH can easily be ascertained by cross-checking the individual ID numbers (given to each neonate in Israel) with the obligatory Cancer Registry of the Israel Ministry of Health, Death Registry of the Ministry of Interior and the Diabetes Registry of the Israeli CDC. The same can be done for the control groups.

At baseline evaluation (age 6-12 months), and re-evaluation time points at 18-24 and 30-36 months of age (and optionally at the age of 5.5 years), the infants are administered tests including Bayley Scales of Infant Development (BSID-III), formal physical & neurological examination, Pediatric Quality of Life scale, Achenbach Child Behavior Checklist and, optionally, a Wechsler Preschool and Primary Scale of Intelligence (WPPSI) test at a further time point, as summarized in Table 1.

At the end of the experiment, each parameter (i.e., physical & neurological assessments, Bayley Scales of Infant Development (BSID-III) scores, Pediatric Quality Of Life scale scores, Achenbach Child Behavior Checklist scores and WPPSI scores) are compared between GH-treated groups and control groups. The inventors expect a significant improvement of neurological, psychological and cognitive scores in the treated group as compared to the control group.

TABLE 1

A summary of the experiment timeline
Study timeline:

$1^{st}$ evaluation - Baseline (6-12 months)

Demographic and medical history questionnaires.
Socioeconomic questionnaire
Formal physical & neurological examination
Bayley Scales of Infant Development (BSID-III)
$2^{ed}$ evaluation (18-24 months)

Bayley Scales of Infant Development (BSID-III)
Formal physical & neurological examination
Pediatric quality of life scale
$3^{ed}$ evaluation (30-36 months)

Bayley Scales of Infant Development (BSID-III)
Formal physical & neurological examination
Pediatric quality of life scale
Achenbach Child Behavior Checklist
$4^{th}$ evaluation (5.5 years), optional The Wechsler Preschool and Primary Scale of Intelligence (WPPSI)

The invention claimed is:

1. A method for the treatment, amelioration, delaying the onset or prophylaxis of small-for-gestational-age (SGA)-associated disorders, diseases, conditions and sequelae, the method comprising the step of administering to an SGA human subject in need thereof a therapeutically effective amount of at least one compound selected from the group consisting of growth hormone (GH), a GH functional fragment, a GH functional mutant, Insulin-like growth factor-I (IGF-I), GH releasing hormone (GHRH), GH releasing peptide 2 (GHRH-2), GH releasing peptide 6 (GHRH-6), Hexarelin, Ghrelin, triiodothyronine (T3), testosterone, isoflavones, capsaicin, casein, bovine colostrum and zinc, wherein said administration is initiated when said human subject is under two years of age.

2. The method according to claim 1, wherein said SGA-associated disorders, diseases and sequelae are at least one of neurological, psychological, cognitive and behavioral damage, disorders or conditions.

3. The method according to claim 2, wherein said SGA-associated disorders, diseases and sequelae further comprise at least one of weight, height and head circumference being under at least 2 standard deviations (SD).

4. The method according to claim 1, wherein said SGA human subject is of an age selected from the group consisting of: about two months to about two years old; about three months to about one year old; and about six months to about one year old.

5. The method according to claim 1, wherein said human subject did not present a catch up growth at the age of about six months and said human subject birth weight was between about 1200 to about 2200 grams.

6. The method according to claim 1, wherein said human subject presents with symmetrical SGA.

7. The method according to claim 1, wherein said treatment improves at least one of Bayley Scales of Infant Development examination score, formal neurological examination score, Pediatric Quality of Life Inventory score and Achenbach Child Behavior Checklist score.

8. The method according to claim 1, wherein said administration is continued for duration of between about one to about five years, preferably said administration is continued for duration of up to two years.

9. The method according to claim 1, wherein said therapeutically effective amount ranges between about 20 μg/kg/day to about 50 μg/kg/day, more preferably about 25 to about 35 g/kg/d.

10. The method of claim 1, wherein the age of the human subject is selected from the group consisting of about 6 months old, about 1 year old, and about 1.5 years old.

11. The method of claim 1, wherein the compound is selected form the group consisting of GH, a functional fragment of GH, a functional mutant of GH, and IGF-1.

\* \* \* \* \*